(12) United States Patent
Benson

(10) Patent No.: US 7,145,145 B2
(45) Date of Patent: Dec. 5, 2006

(54) OPTICAL WINDOW FOR MONITORING SAMPLES

(75) Inventor: Ian Beethom Benson, Maldon (GB)

(73) Assignee: NDC Infrared Engineering, Ltd. (GB)

( * ) Notice: Subject to any disclaimer, the term of this patent is extended or adjusted under 35 U.S.C. 154(b) by 306 days.

(21) Appl. No.: 10/489,985

(22) PCT Filed: Sep. 13, 2002

(86) PCT No.: PCT/GB02/04195

§ 371 (c)(1),
(2), (4) Date: Mar. 17, 2004

(87) PCT Pub. No.: WO03/025550

PCT Pub. Date: Mar. 27, 2003

(65) Prior Publication Data

US 2004/0232340 A1    Nov. 25, 2004

(30) Foreign Application Priority Data

Sep. 20, 2001 (GB) ................................. 0122711.5

(51) Int. Cl.
*G01J 5/02* (2006.01)
(52) U.S. Cl. ................................................. 250/339.07
(58) Field of Classification Search ........... 250/339.07, 250/336.1
See application file for complete search history.

(56) References Cited

U.S. PATENT DOCUMENTS

| 4,260,262 A | 4/1981 | Webster |
| 4,622,465 A | 11/1986 | Harig et al. |
| 5,161,055 A | 11/1992 | Blechschmidt |
| 5,324,949 A | 6/1994 | Johnsen |
| 5,563,737 A * | 10/1996 | Kamrat ........................ 359/509 |
| 6,281,498 B1 | 8/2001 | Fellows |
| 6,426,794 B1 * | 7/2002 | Trainoff ....................... 356/246 |

FOREIGN PATENT DOCUMENTS

| CH | 591078 | 8/1977 |
| GB | 1567031 | 5/1980 |
| GB | 2332756 | 6/1999 |
| JP | 1-100272 | 4/1989 |
| JP | 8-278248 | 10/1996 |
| JP | 11-118714 | 4/1999 |
| JP | 11-288870 | 10/1999 |
| WO | WO 89/09388 | 10/1989 |

(Continued)

*Primary Examiner*—David Porta
*Assistant Examiner*—Christopher Webb
(74) *Attorney, Agent, or Firm*—Andrus, Sceales, Starke & Sawall, LLP

(57) ABSTRACT

The invention is concerned with a material processing apparatus, e.g. a dryer such as a fluid bed dryer, for processing material, e.g. pharmaceuticals, in a compartment (12) having a wall (10). The wall has a window for transmitting radiation from an infrared spectrometer (30) into the dryer and for transmitting radiation from the material to the spectrometer. The spectrometer (30) can analyze the radiation transmitted from the material to measure a property of the material within the compartment, e.g. its moisture content. The radiation-transmitting element (28) is present in a moveable body (24), e.g. a sphere, that can be moved to bring the element (28) into a second position (31) in which the element is in contact with a duct (40) through which fluid can be passed to clean the element (28). In addition, a wiper member (34) may be provided that wipes the element (28) as it passes over it as the moveable body (26) is moved into the second position.

23 Claims, 3 Drawing Sheets

FOREIGN PATENT DOCUMENTS

| | | | | | |
|---|---|---|---|---|---|
| WO | WO 98/22806 | 5/1998 | WO | WO 01/25153 | 4/2001 |

* cited by examiner

OPTICAL WINDOW FOR MONITORING SAMPLES

CROSS REFERENCE TO RELATED APPLICATION

The present application is the U.S. national stage application of International Application PCT/GB02/04195, filed Sep. 13, 2002, which international application was published on Mar. 27, 2003 as International Publication WO 03/025550. The International Application claims priority of British Patent Application 0122711.5, filed Sep. 20, 2001.

TECHNICAL FIELD

The present invention relates to optical sampling windows in apparatus for processing materials, e.g. dryers and granulators, and especially for use in monitoring material being processed using optical measuring techniques, for example infrared spectroscopy. As used in the present specification and claims, the terms "optical" and "radiation" are intended to refer to non-visible parts of the spectrum, for example infrared radiation, in addition to visible radiation.

BACKGROUND ART

Pharmaceuticals and other materials are often dried in fluid bed dryers and it is known to monitor the progress of the drying using an infrared spectrometer (commonly referred to as a "gauge"). The gauge projects a beam of infrared radiation through a window in the wall of the dryer and measures the light reflected by the material being dried. The radiation directed into the dryer includes (a) a wavelength that is absorbed by water and (b) a wavelength that is not absorbed by water or the material. The intensity of radiation reflected back by the material being dried in the wavelength that is absorbed by water will be reduced as a result of absorption by water in the material in comparison to the intensity of the reflected radiation in wavelengths that are not absorbed. The intensity of light at that wavelength increases as the amount of water in the material decrease. By comparing the intensity of the radiation at the absorbed wavelength with that at non-absorbed wavelengths, it is possible to measure the amount of water in the pharmaceutical and assess when it is dry. The window should have a high transmission for radiation in all the wavelengths being used for measurement.

Suitable infrared gauges for such an application are well known and are manufactured by the Applicant Company. An example of such a gauge is described in published PCT application no. WO98/22806. However, the precise details of the gauge do not form part of the present invention.

WO01/25153 describes a radiation sensor mounted in a cylindrical body for sensing radiation from a source. The sensor is mounted in a channel with the axis of the cylindrical body lying at right angles to the axis of the channel. The cylindrical body can be rotated through 180° to a position facing away from the radiation source so that the sensor can be cleaned.

JP-11-288870 describes a system for cleaning lenses. Two sets of lenses are provided on a rotatable housing. When one set of lenses is in use, the other is located at a cleaning station. The housing can be rotated to bring the lenses that were previously in use into the cleaning station and vice versa for the other set of lenses. Such an arrangement doubles the cost of the lenses.

GB-1567031 describes a sensor for sensing the turbidity of a liquid and includes a light source and a light sensor. The light source and light sensor can be moved into a retracted position past wiper blades to clean any deposits on the light transmitting housing containing the sensor and/or light source.

GB-2332756 describes a camera attachment for location in front of the camera lens. It consists of a disc that is rotated at high speed to remove any moisture that may gather on it.

WO89/09388 describes a near infrared analysis device of material held in a test chamber, which has an opening through which infrared radiation can pass. A ribbon of infrared transparent material is pressed against the opening to form a window. Between successive samples, the ribbon is advanced so that a fresh piece of ribbon forms the window in each successive test.

U.S. Pat. No. 5,161,055 describes a rotating inspection window that spins at such a speed that water or other debris falling on the window is slung off by centrifugal force.

U.S. Pat. No. 4,260,262 describes a grain quality analyser in which the grain is successively exposed to radiation of different wavelengths, including infrared.

CH-591078 describes a device for measuring the purity of a liquid flowing through a pipe. Part of the pipe is replaced by a light-transmitting sleeve that enables the liquid flowing through the sleeve to be analysed photometrically. Wiper blades are provided on the inside of the sleeve and the sleeve is rotated so that the blades wipe the inside of the sleeve clean.

JP-11118714 describes a system for measuring turbidity having a light source and a light sensor. A disc is rotated between the source and the sensor.

JP-1100272 descibes a vapour deposition apparatus having an energy source that decomposes reaction gas. The radiation source is located within a cylindrical transparent window that is rotated so that part of its circumference is located in a vapour deposition chamber and part in a cleaning chamber.

JP-827824 describes a powder treatment apparatus having a light transmitting window in the form of a rotatable cylinder that can be rotated past a wiper to clean the drum surface.

One severe disadvantage that limits the use of infrared gauges in the monitoring of materials being dried in fluid bed and other dryers is that the material can be sticky, particularly when moist. It can therefore adhere to the window and prevent radiation from passing into the interior of the dryer. Since, in these circumstances, it is not possible to monitor the water content of the material being dried, the drying may have to be stopped in order to allow the window to be cleaned.

The present invention is intended to overcome the above problem.

DISCLOSURE OF INVENTION

According to the present invention there is provided an optical window that can be secured in a wall of a material-processing apparatus to derive information about the stage of processing of the material in the apparatus, wherein the optical window comprises:

a radiation-transmitting element that is capable of transmitting radiation along an axis into the apparatus and for transmitting radiation along the axis out of the apparatus, the light emanating from the material being processed, whereby radiation transmitted out of the apparatus can be analysed to measure the progress of the processing of the material within the apparatus, a moveable body carrying the radiation-transmitting element, the body being moveable between a first position in which the element can transmit radiation into and out of the apparatus and a second position in which the element can be cleaned; and a cleaning chamber lying adjacent to the element when the moveable body is in the second position, whereby the element can be cleaned by contacting it with a fluid in the cleaning chamber.

The present invention also comprises a material processing apparatus, e.g. a granulator or a dryer such as a fluid bed dryer, that includes such an optical window and a method of processing material using the above window to monitor the progress of the processing.

The chamber is preferably a duct through which the cleaning fluid can be passed to clean the radiation-transmission element located adjacent to and in contact with the interior of the duct. The fluid will generally be a liquid solvent that will dissolve the material sticking to the radiation-transmitting element, i.e. the material being processed. It is conceivable that the element might be able to be cleaned by a gas, for example a blast of dry air. If a solvent is used, the duct is preferably also connectable to a source of gas to dry the element after cleaning and before it is returned to its normal (first) position transmitting radiation into and out of the apparatus.

In addition, the cleaning of the optical radiation-transmitting element may be brought about by a wiper member that passes over and wipes the element as it is moved between the first and the second positions. In extreme cases; the moveable body may be moved to expose the radiation-transmitting element to the outside thereby allowing it to be cleaned manually.

The material processing apparatus is preferably a dryer and the property being measured is preferably the content of a volatile material, e.g. water, in the material being dried.

The invention is applicable to the processing of pharmaceuticals and foodstuffs, e.g. milk products such as milk powders and dried cheese; it can be used to remove not only water but also other volatile materials, e.g. solvents.

BRIEF DESCRIPTION OF THE DRAWINGS

A sampling window according to the present invention will now be described, by way of example only, with reference to the following drawings in which.

DESCRIPTION OF THE BEST MODE FOR IMPLEMENTING THE INVENTION

Figure 1:
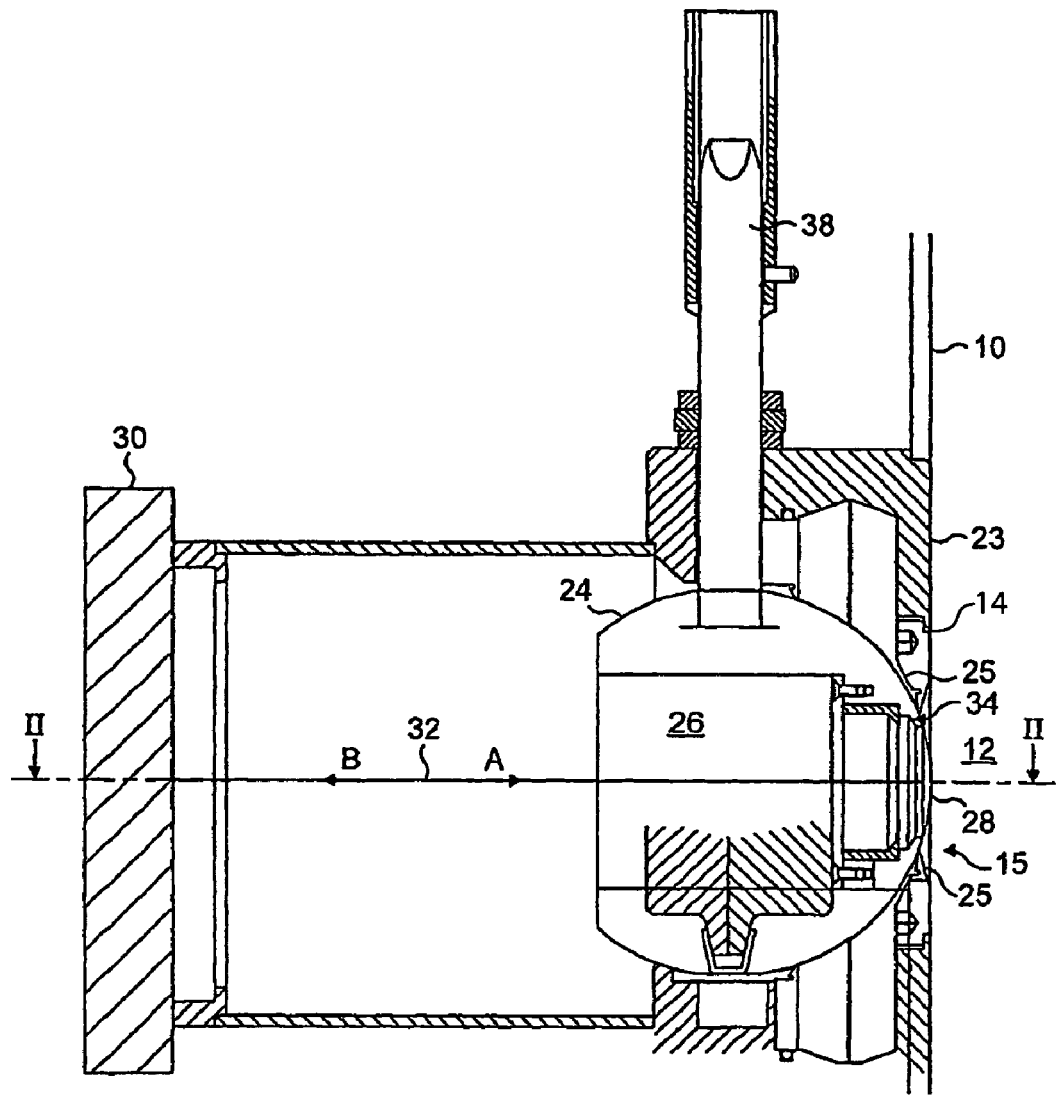
FIG. 1 is a sectional view taken through the wall of a dryer and through an optical window of the present invention.

Referring initially to FIG. 1, there is shown the wall 10 of a dryer. Material to be dried is located in a drying compartment 12 (only part of the compartment is shown). The wall 10 has an opening 14 and an optical sampling window 15 according to the present invention extends across the opening. The window includes a socket 23 holding a sphere 24 containing a bore 26. The bore 26 is closed at one end by a radiation-transmitting element 28 which is located in contact with the dryer compartment 12, as shown in FIG. 1. PTFE seals 25 close the gaps between the spherical holder 24 and the wall 10.

An infrared spectrometer ("gauge") is indicated schematically by block 30 and is located on the outside of the dryer compartment 12 on the axis 32 of the bore 26; the gauge can transmit infrared radiation in the direction of arrow A through the bore 26 and through the optical element 28 into the interior compartment 12 of the dryer. Likewise, radiation reflected by material within the compartment 12 can pass back along the same path in the direction of arrow B to the gauge 30. The radiation should contain at least two wavelengths, which may be transmitted by the gauge simultaneously or sequentially, namely a wavelength that is substantially absorbed by water and a wavelength that is not substantially absorbed by water. In this way, as is known, the moisture of the material within the dryer can be monitored by the gauge by assessing the relative intensities of the reflected radiation at the two wavelengths. The drying process is stopped when the moisture content of the material has dropped to the desired level.

Materials within the compartment 12 can adhere to the outside of the radiation-conductive element 28 and obscure the optical path of the gauge 30. In order to clean this adherent material off, the sphere 24 may be rotated so that the lip 34 of the seal 25 wipes over the optical element 28 and removes adhering material. Since the seal 25 is made of PTFE, the friction between the lip and the element is minimised while allowing close contact between the lip and the element to clean it. Other alternative arrangements for wiping the element can be used.

The above arrangement only removes large adhering particles but does not remove small particles and films. Accordingly, the sphere can be rotated though 52° by a shaft 38 (see FIG. 1) to the position shown in outline 31 in FIG. 2, in which the element 28' is located in a chamber 40, which runs annually around the sphere. The seal 25 along with seal 27 isolate the chamber 40 from the inside of the drying chamber and the bore (respectively).

The chamber 40 is formed in two parts that are held together around the sphere 24 by a clamp 42, which can be released by the handle 56.

Figure 2:
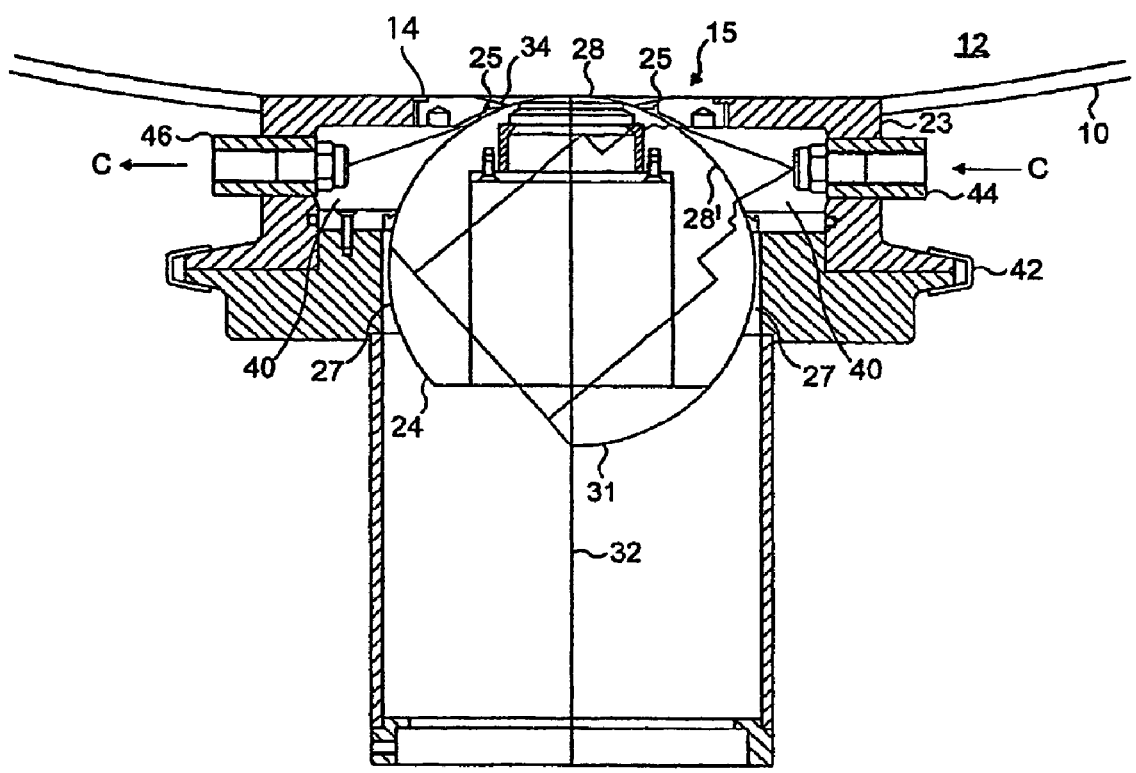
FIG. 2 is a sectional view of the dryer wall and the window of the present invention taken along line II—II shown in FIG. 1.
Figure 3:
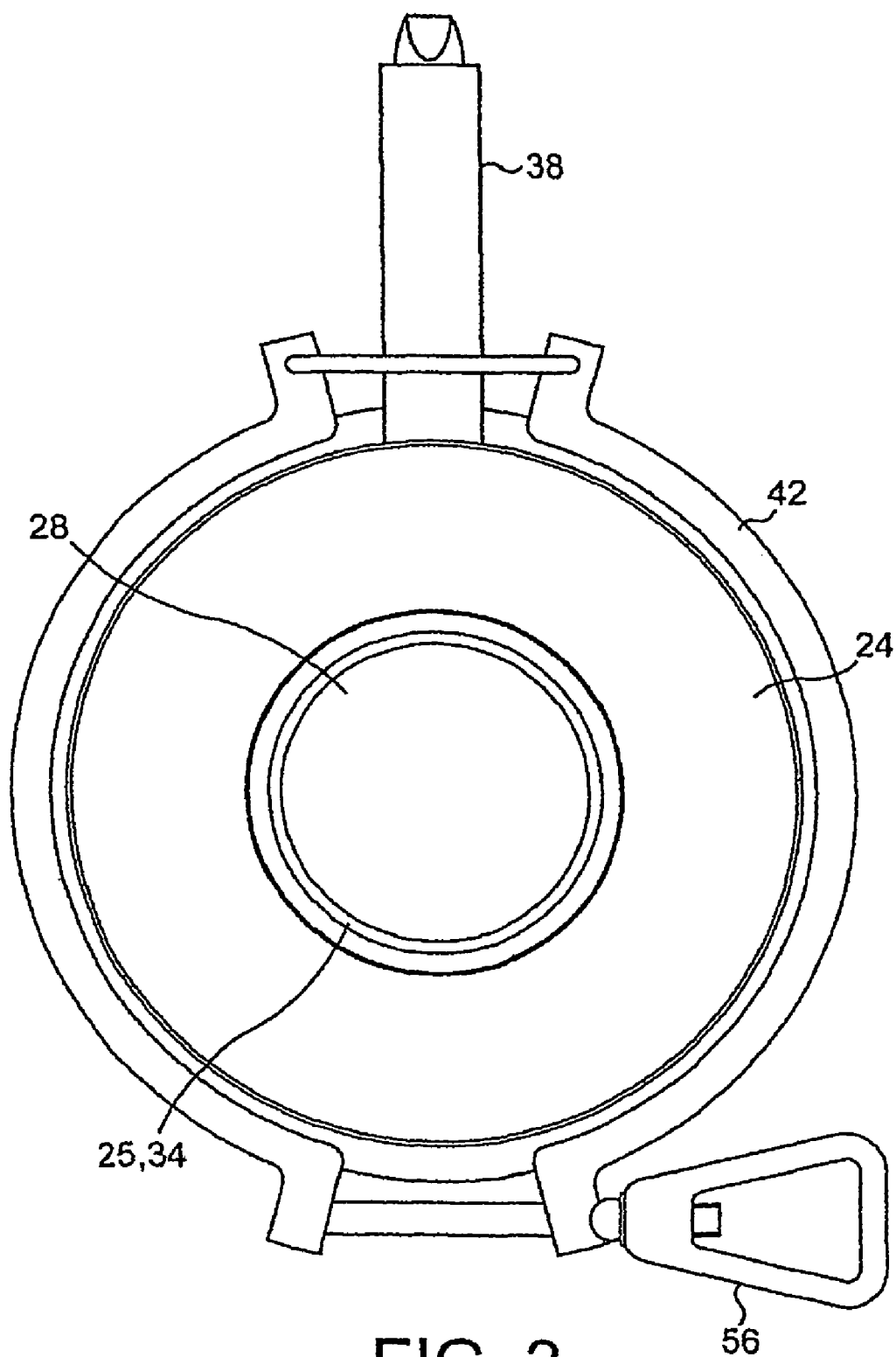
FIG. 3 is a front elevation of the optical window of FIGS. 1 and 2 viewed in the direction of arrow "A" in FIG. 1 but without the infrared gauge 30.

Water or other solvent for the material being dried in the dryer is passed into the annular chamber 40 through a nipple 44 and passes out of the chamber through a second nipple 46 as shown by arrows C in FIG. 2, cleaning the element as it passes through the chamber. After the solvent has passed, a drying gas, e.g. warm air, is passed through annular chamber 40 to dry the element 28. Once the cleaning has been accomplished the sphere 24 is rotated back to the position shown in FIG. 1 in which the bore is aligned with the optical axis 32.

The materials used for making the sphere 24 and the element 28 should be compatible with the material being dried and with any regulations governing the processing of such material. In the case of pharmaceuticals, the sphere 24 is preferably made of stainless steel and the element 28 is preferably made of sapphire.

It will be appreciated that the holder for carrying the radiation-transmitting element may have a shape other than a sphere that will allow it to rotate within a socket, for example it may be cylindrical. Alternatively the element may be provided on a wheel (not shown) that can be rotated or on a slide (not shown) that can be slid to bring the element 28 into contact with a cleaning chamber.

The solvent and air are supplied to and drained from the annular chamber 40 via lines (not shown) extending from the nipples 44, 46 to an outside solvent reservoir and discharge line.

In the initial stages of drying the material in the dryer, when the material is at its most sticky, the dryer may advantageously be operated with the sphere 24 in the position shown in outline 31 in FIG. 2, since the amount of water present will be known to be high and so a reading from the gauge 30 is unnecessary; in position 31, the material will self-evidently not adhere to the element 28. After a time in which the operator knows through experience that the material will be partially dry, he/she can rotate the sphere to the position shown in FIG. 1 in which the element 28 is in contact with the drying compartment for monitoring the drying procedure in the final stages of drying, when the material will be less sticky. Such a regime will reduce the number of times that the element 28 needs to be washed in the course of a drying cycle.

The invention claimed is:

1. An optical window that can be secured in a wall of a material-processing apparatus to derive information about the stage of processing of the material in the apparatus, wherein the optical window comprises:
   a radiation-transmitting element that is capable of transmitting radiation along an axis into the apparatus and for transmitting radiation along the axis out of the apparatus, the light emanating from the material being processed, whereby radiation transmitted out of the apparatus can be analysed to measure the progress of the processing of the material within the apparatus,
   a moveable body carrying the radiation-transmitting element, the body being moveable between a first position in which the element can transmit radiation into and out of the apparatus and a second position in which the element can be cleaned;
   a cleaning chamber that, when the moveable body is in the second position, lies adjacent to the element whereby the element can be cleaned by contacting with a fluid in the cleaning chamber.

2. An optical window as claimed in claim 1, wherein the cleaning chamber is a duct through which the cleaning fluid can be passed.

3. An optical window as claimed in claim 2, wherein the duct extends wholly or partially around the element.

4. An optical window as claimed in claim 3, wherein the duct lies in a plane that is transverse to the axis.

5. An optical window as claimed in claim 4, wherein the duct lies in a plane that is orthogonal to the axis.

6. An optical window as claimed in claim 1, wherein the cleaning chamber is connectable to a source of solvent for the material being dried and to a source of gas to dry the radiation-transmitting element after cleaning.

7. An optical window as claimed in claim 1, which includes a wiper member past which the radiation-transmitting element passes when the moveable body is moved between the first and second positions.

8. An optical window as claimed in claim 1, wherein the moveable body is rotatable.

9. An optical window as claimed in claim 8, wherein the moveable body is a sphere.

10. An optical window as claimed in claim 8, wherein the moveable body is a cylinder or wheel.

11. A material processing apparatus, e.g. a granulator or a dryer such as a fluid bed dryer, comprising a compartment for processing material, a wall defining the compartment, an opening in the wall and an optical window as claimed in claim 1 secured across the opening.

12. An apparatus claimed in claim 11, which includes an infrared spectrometer to transmit infrared radiation through the radiation-transmitting element into the interior of the material processing compartment and to collect infrared radiation transmitted back through the radiation-transmitting element.

13. A method of measuring a property of material being processed within a material-processing apparatus, which method comprises transmitting radiation along an axis from outside of the apparatus through a radiation-transmitting element onto material within the apparatus, collecting radiation emanating from the material through the radiation-transmitting element to the outside of the compartment and measuring a property of the material being processed by analysing the radiation emanating from the material, wherein the radiation-transmitting element is present in a moveable body and the method further includes moving the moveable body to bring the radiation-transmitting element into contact with a chamber containing a cleaning fluid and washing the radiation-transmitting element with the fluid.

14. A method as claimed in claim 13 wherein the optical window includes a wiper member and the method includes moving the moveable body so that the radiation-transmitting element passes over, and is wiped by, the wiper member.

15. A method as claimed in claim 14 wherein the chamber is a duct and the method includes passing the cleaning fluid through the duct to clean the radiation-transmitting element.

16. A method as claimed in claim 13 wherein the chamber is a duct and the method includes passing the cleaning fluid through the duct to clean the radiation-transmitting element.

17. A method as claimed in claim 16, wherein the duct extends wholly or partially around the element.

18. A method as claimed in claim 17, wherein the duct lies in a plane that is transverse to the axis.

19. A method as claimed in claim 18, wherein the duct lies in a plane that is orthogonal to the axis.

20. A method as claimed in claim 16, wherein the cleaning fluid is a liquid and the method includes the additional step of passing a gas through the duct to dry the radiation-transmitting element after cleaning.

21. A method as claimed in claim 13, wherein the property being measured is the content of a volatile material in the material being processed.

22. A method as claimed in claim 13, wherein the material is a pharmaceutical or foodstuff.

23. A method as claimed in claim 13, wherein the radiation transmitted from the outside of the optical window through the radiation-transmitting element onto the material within the drying compartment is at an infrared wavelength.

* * * * *